United States Patent
Zhang et al.

(10) Patent No.: US 11,931,742 B2
(45) Date of Patent: Mar. 19, 2024

(54) CARRYING MODULE, NUCLEIC ACID LOADING DEVICE AND USE THEREOF

(71) Applicant: GENEMIND BIOSCIENCES COMPANY LIMITED, Shenzhen (CN)

(72) Inventors: Songzhen Zhang, Shenzhen (CN); Zefei Jiang, Shenzhen (CN); Guangming Wang, Shenzhen (CN); Ping Wu, Shenzhen (CN); Zhiliang Zhou, Shenzhen (CN); Qin Yan, Shenzhen (CN)

(73) Assignee: GENEMIND BIOSCIENCES COMPANY LIMITED (CN)

( * ) Notice: Subject to any disclaimer, the term of this patent is extended or adjusted under 35 U.S.C. 154(b) by 924 days.

(21) Appl. No.: 16/960,748

(22) PCT Filed: Dec. 12, 2018

(86) PCT No.: PCT/CN2018/120525
§ 371 (c)(1),
(2) Date: Jul. 8, 2020

(87) PCT Pub. No.: WO2019/144717
PCT Pub. Date: Aug. 1, 2019

(65) Prior Publication Data
US 2020/0338564 A1    Oct. 29, 2020

(30) Foreign Application Priority Data
Jan. 23, 2018  (CN) .......................... 201810063798.2

(51) Int. Cl.
*B01L 7/00*    (2006.01)
*B01L 3/00*    (2006.01)
(Continued)

(52) U.S. Cl.
CPC ......... *B01L 7/525* (2013.01); *B01L 3/502715* (2013.01); *B01L 3/50273* (2013.01);
(Continued)

(58) Field of Classification Search
CPC ............... B01L 7/525; B01L 3/502715; B01L 3/50273; B01L 9/523; B01L 2200/16;
(Continued)

(56) References Cited

U.S. PATENT DOCUMENTS

2005/0188705 A1*  9/2005  Jones ...................... F25B 9/002
                                                    62/401
2012/0270305 A1* 10/2012  Reed ................... G01N 35/1079
                                                    422/560
(Continued)

FOREIGN PATENT DOCUMENTS

CN    103793627 A    5/2014
CN    205590713 U    9/2016
(Continued)

OTHER PUBLICATIONS

European Search Report in related Application No. EP18901946.6, dated Sep. 27, 2021, 7 pages.
(Continued)

*Primary Examiner* — Benjamin R Whatley
(74) *Attorney, Agent, or Firm* — Dilworth IP, LLC

(57) ABSTRACT

A nucleic acid loading device, including a housing, a carrying module, a motion module, a liquid circuit module and a control module. The motion module includes a support platform, first and second driving mechanisms, and a carrying member. The liquid circuit module is configured to control a reagent to flow into and out of a reactor. The control module is connected with the motion module and the liquid circuit module, and the control module is configured to control the first and second driving mechanisms, the
(Continued)

liquid circuit module and the temperature control unit. A first face of a semiconductor cooler heats or refrigerates during operation, providing heat for an accommodating seat through a heat conducting body such that the reactor can be at different ambient temperatures. The cooperation between the motion and liquid circuit modules may achieve automation and industrialization of loading a sample into the reactor.

18 Claims, 9 Drawing Sheets

(51) Int. Cl.
  *B01L 9/00* (2006.01)
  *C12Q 1/6806* (2018.01)
(52) U.S. Cl.
  CPC .............. *B01L 7/52* (2013.01); *B01L 9/523* (2013.01); *C12Q 1/6806* (2013.01); *B01L 2200/147* (2013.01); *B01L 2200/148* (2013.01); *B01L 2200/16* (2013.01); *B01L 2300/041* (2013.01); *B01L 2300/06* (2013.01); *B01L 2300/0627* (2013.01); *B01L 2300/1805* (2013.01); *B01L 2300/185* (2013.01); *B01L 2300/1894* (2013.01); *B01L 2400/0487* (2013.01); *B01L 2400/049* (2013.01)
(58) Field of Classification Search
  CPC ........... B01L 2300/041; B01L 2300/06; B01L 2300/0627; B01L 2300/1805; B01L 2300/1894; B01L 2400/0487; C12Q 1/6806
  See application file for complete search history.

(56) References Cited

U.S. PATENT DOCUMENTS

| | | | |
|---|---|---|---|
| 2014/0092933 A1 | 4/2014 | Coursey et al. | |
| 2014/0208772 A1* | 7/2014 | Schon | F25B 21/04 62/3.3 |
| 2016/0380710 A1 | 12/2016 | Huang et al. | |
| 2018/0251833 A1* | 9/2018 | Daugharthy | C12Q 1/68 |
| 2019/0058101 A1* | 2/2019 | Oi | H10N 10/855 |

FOREIGN PATENT DOCUMENTS

| | | | | |
|---|---|---|---|---|
| CN | 205590715 U | | 9/2016 | |
| CN | 106096332 A | | 11/2016 | |
| CN | 106967600 A | * | 7/2017 | ........... C12Q 1/6869 |
| CN | 106967600 A | | 7/2017 | |
| CN | 206457488 U | * | 9/2017 | |
| CN | 206457488 U | | 9/2017 | |
| CN | 108018195 A | * | 5/2018 | ........ B01L 3/502715 |
| CN | 108018195 A | | 5/2018 | |
| CN | 207998608 U | | 10/2018 | |
| CN | 208055315 U | | 11/2018 | |
| JP | 2012052830 A | | 3/2012 | |
| WO | WO-2017079406 A1 | * | 5/2017 | .............. C12Q 1/68 |
| WO | 2017123864 A1 | | 7/2017 | |

OTHER PUBLICATIONS

International Search Report issued in International Application No. PCT/CN2018/120525, dated Mar. 14, 2019, 2 pages.

* cited by examiner

CARRYING MODULE, NUCLEIC ACID LOADING DEVICE AND USE THEREOF

CROSS REFERENCE TO RELATED APPLICATION

This application claims priority to Chinese Patent Application No. 201810063798.2, filed on Jan. 23, 2018, the entire content of which is incorporated herein in its entirety.

FIELD OF THE INVENTION

The present disclosure relates to a field of biological sample processing apparatuses, and more particularly, to a carrying module and a nucleic acid loading device and use thereof.

BACKGROUND

At present, in tests of detecting biological macromolecules based on solid-phase chip detection, a sample to be detected needs to be connected to a chip surface. For example, a probe (oligonucleotide) is fixed on a chip, and then nucleic acids to be detected are connected to the probe by hybridization, such that the nucleic acids to be detected are connected to the chip.

For example, in a platform for sequencing nucleic acids using chip detection, before an on-machine test, the nucleic acid molecules to be detected generally need to be loaded on a reactor, such as by binding to a chip with a probe fixed on its surface through hybridization, and then the reactor containing the sample to be detected is placed on the sequencing platform for sequencing.

In the related art, different reaction temperatures and conditions are often required in the process of loading nucleic acids with the probe and the sequence to be detected onto the reactor. It is worth paying attention to how to provide the process with a good temperature environment and achieve automation and industrialization of the process.

SUMMARY

The present disclosure provides a carrying module, a nucleic acid loading device and use thereof.

The nucleic acid loading device according to embodiments of the present disclosure includes a carrying module, a motion module, a liquid circuit module and a control module. The carrying module includes an accommodating seat and a temperature control unit, the nucleic acid is loaded in a reactor, and the accommodating seat is configured to accommodate the reactor. The temperature control unit includes a semiconductor cooler, a heat conducting body and a temperature sensor. The semiconductor cooler includes a first face and a second face opposite to each other. The heat conducting body is connected with the first face and the accommodating seat. The temperature sensor is arranged in the heat conducting body and used to detect the temperature of the heat conducting body.

The motion module includes a partition plate, a support platform, a first driving mechanism, a carrying member and a second driving mechanism. The support platform is detachably and movably arranged on the partition plate. The first driving mechanism is fixed on the partition plate and is configured to drive the support platform to move along a first direction relative to the partition plate. The second driving mechanism is fixed on the support platform and is configured to drive the carrying member to move along a second direction relative to the support platform. The second direction is perpendicular to the first direction.

The liquid circuit module is configured to control a reagent to flow into and out of the reactor, and the liquid circuit module includes an injection pump configured to provide negative pressure.

The control module is connected with the carrying module, the motion module and the liquid circuit module, and is configured to control the operation of the first driving mechanism, the second driving mechanism, the liquid circuit module and the temperature control unit.

The carrying module in embodiments of the present disclosure includes: an accommodating seat provided with an accommodating groove for accommodating a reactor, the accommodating seat being provided with a through-hole in communication with the accommodating groove; a semiconductor cooler comprising a first face and a second face opposite to each other; and a heat conducting body connected with the first face and the accommodating seat.

The embodiments of the present disclosure also provide a nucleic acid loading device including a carrying module according to any of the above embodiments.

In the carrying module and the nucleic acid loading device according to the embodiments of the present disclosure, the first face of the semiconductor cooler heats or refrigerates during operation, thereby providing heat for the accommodating seat through the heat conducting body such that the reactor can be at different ambient temperatures. In addition, the design of the structural connection of the carrying module, the motion module and the liquid circuit module, as well as the cooperation with the control module, can achieve the automation and industrialization of the process of loading samples to be detected into the reactor, with simple operation and consistent and controllable operation results.

The present disclosure also provides the use of the above nucleic acid loading device in nucleic acid immobilization and/or hybridization.

Additional aspects and advantages of embodiments of present disclosure will be given in part in the following descriptions, become apparent in part from the following descriptions, or be learned from the practice of the embodiments of the present disclosure.

BRIEF DESCRIPTION OF THE DRAWINGS

These and/or other aspects and advantages of the present disclosure will become apparent and readily appreciated from the following descriptions of embodiments made with reference to the drawings, in which.

Figure 1:
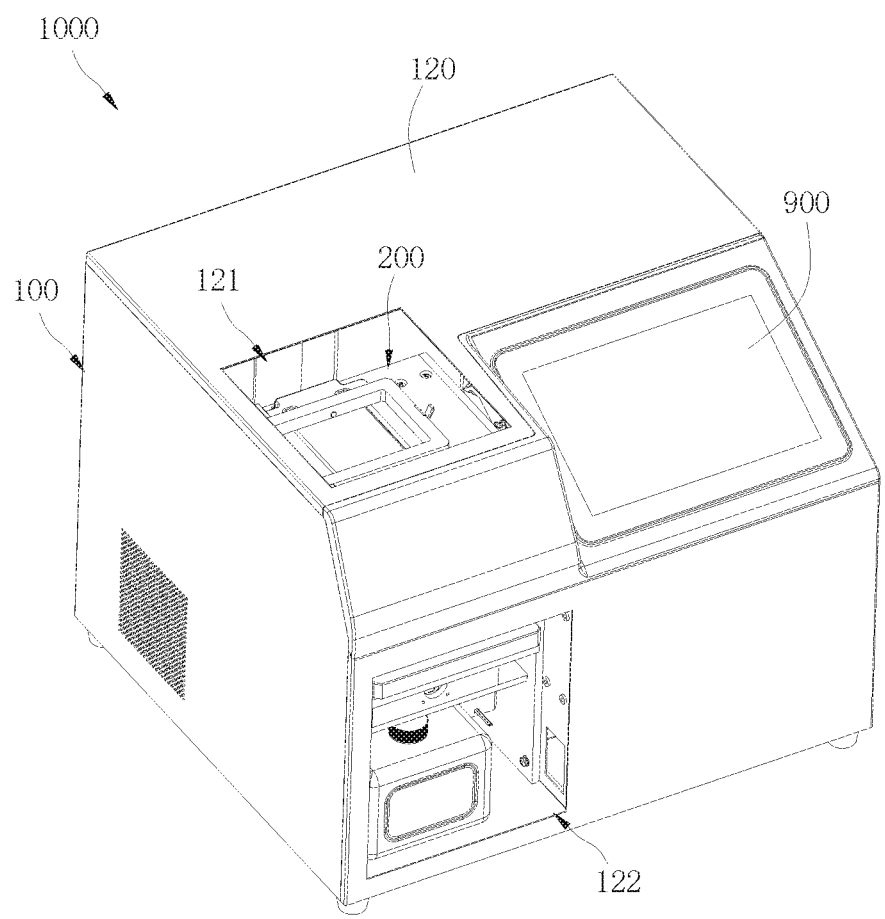
FIG. 1 illustrates a perspective view of a sample processing device according to an embodiment of the present disclosure.
Figure 2:
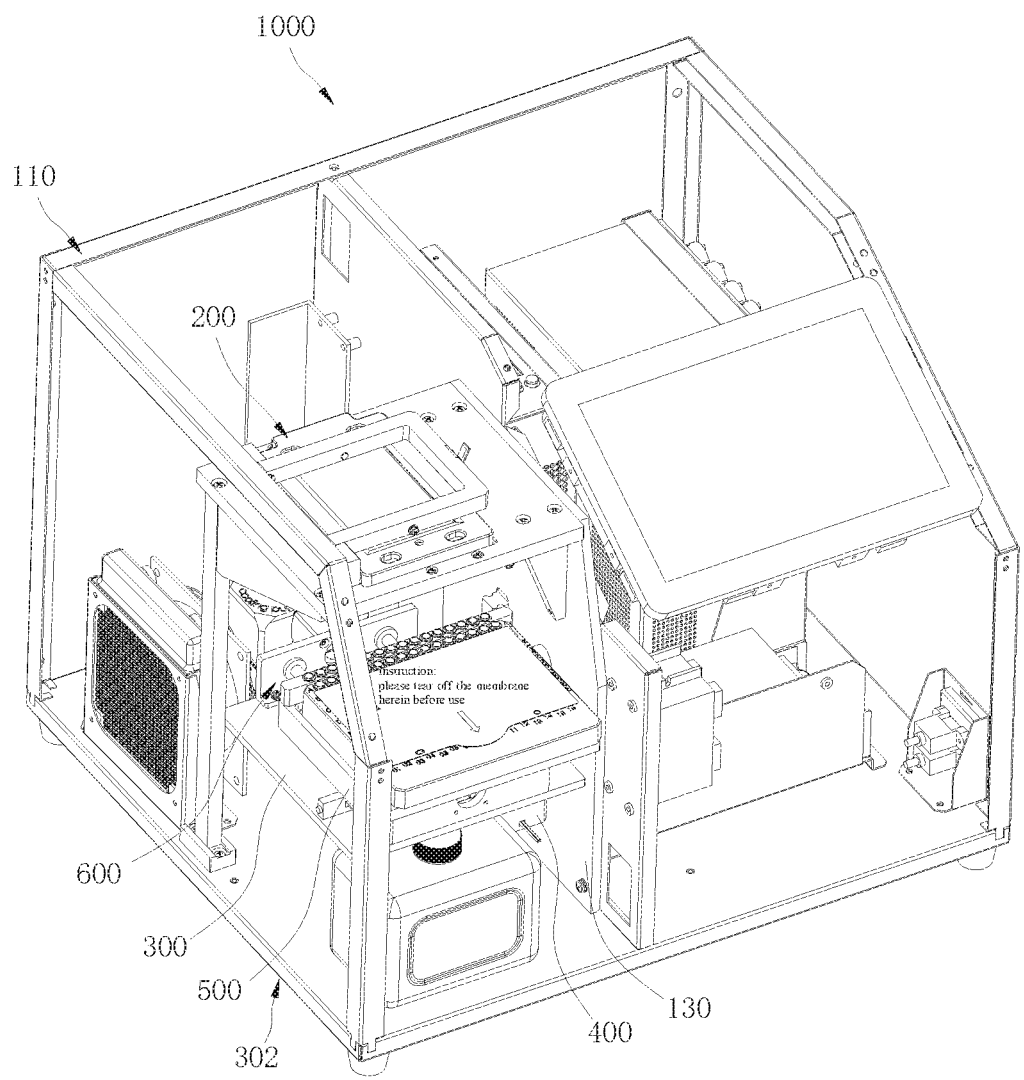
FIG. 2 illustrates a schematic view of an internal structure of a sample processing device according to an embodiment of the present disclosure.
Figure 3:
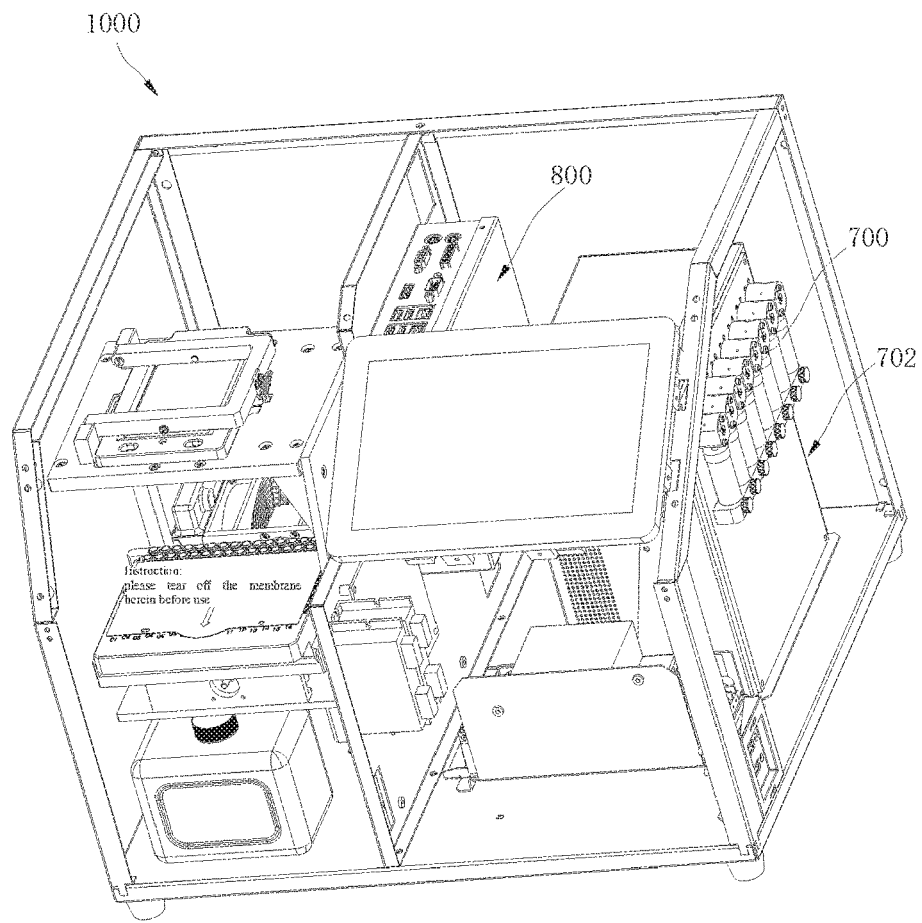
FIG. 3 illustrates another schematic view of an internal structure of a sample processing device according to an embodiment of the present disclosure.

REFERENCE NUMERALS OF MAIN ELEMENTS nucleic acid loading device 1000, housing 100, frame 110, panel 120, first window 121, second window 122, partition plate 130;

carrying module 200, reactor 202, accommodating seat 210, accommodating groove 211, semiconductor cooler 220, first face 221, second face 222, heat conducting body 230, heat dissipating body 240, fin 241, heat dissipating channel 242, cover plate 243, insulating body 250, temperature sensor 260, fixing seat 270, pressing member 280, engaging structure 281, protrusion 282, engaging hole 283, stop member 290;

motion module 302, support platform 300, reagent kit 310, liquid reservoir portion 311, handle portion 312, liquid reservoir groove 313, membrane 314, flange 315;

first driving mechanism 400, first electric motor 410, first transmission shaft 420;

carrying member 500, sliding block 510, bracket 520;

second driving mechanism 600, second electric motor 610, second transmission shaft 620, guide rod 630;

liquid circuit module 702, injection pump 700, control module 800.

DETAILED DESCRIPTION

Embodiments of the present disclosure are described in detail below, examples of which are shown in the accompanying drawings, wherein like or similar reference numerals refer to like or similar elements or elements having the same or similar functions throughout. The embodiments described below with reference to the accompanying drawings are exemplary only and are for the purpose of explaining the disclosure and are not to be construed as limiting the disclosure.

In the present disclosure, unless specified and limited otherwise, a first feature "above" or "below" a second feature may include direct contact and indirect contact of the first and second features. Moreover, the first feature "above" the second feature includes that the first feature is directly above the second feature, obliquely above the second feature, or simply means that the first feature is higher in level than the second feature; likewise, the first feature "below" the second feature includes that the first feature is directly below the second feature, obliquely below the second feature, or simply means that the first feature is less horizontal than the second feature.

In the present disclosure, unless specified or limited otherwise, the terms "mounted," "connected," "coupled," "fixed" and the like are used broadly, and may be, for example, fixed connections, detachable connections, or integral connections; may also be mechanical or electrical connections; may also be direct connections or indirect connections via intervening structures; may also be inner communications of two elements, which can be understood by those skilled in the art in light of specific circumstances.

Referring to FIGS. 1-3 and FIG. 11, according to one embodiment of the present disclosure, a nucleic acid loading device 1000 includes a housing 100, a carrying module 200, a motion module 302, a liquid circuit module 702, and a control module 800.

The motion module 302 includes a support platform 300, a first driving mechanism 400, a carrying member 500, and a second driving mechanism 600. The liquid circuit module 702 includes an injection pump 700 and a conduit (not shown) connected with the injection pump 700. The carrying module 200, the support platform 300, the first driving mechanism 400, the carrying member 500, the second driving mechanism 600, the injection pump 700, and the control module 800 are all located in the housing 100.

The housing 100 includes a frame 110, a panel 120, and a partition plate 130. The panel 120 is arranged on the frame 110. For example, the panel 120 is fixed on the frame 110 by a fastener such as a screw. The frame 110 is partitioned by the partition plate 130 to form a space. In one example, the frame 110 is formed by welding angle steel.

In the present embodiment, the injection pump 700 and the control module 800 are both located on the same side of the partition plate 130, and the carrying module 200, the support platform 300, the first driving mechanism 400, the carrying member 500, and the second driving mechanism 600 are all located on the other side of the partition plate 130.

Specifically, the injection pump 700 is arranged close to the panel 120, and the control module 800 is fixed on the partition plate 130. The panel 120 close to the injection pump 700 may be a transparent panel, such that the user can observe the condition of the injection pump 700 through the panel 120. For example, the user can observe whether there are bubbles in the injection pump 700 through the panel 120. The support platform 300, the first driving mechanism 400, the carrying member 500, and the second driving mechanism 600 are arranged close to each other, and the carrying module 200 is located above the support platform 300.

It could be understood that in other embodiments, positions of the carrying module 200, the support platform 300, the first driving mechanism 400, the carrying member 500, the second driving mechanism 600, the injection pump 700, and the control module 800 may be set in other ways. For example, the control module 800 and the injection pump 700 are located on two opposite sides of the partition plate 130.

It could be understood that the control module 800 includes a memory and a processor. The memory is used to store input data including program instructions, and the processor may run the program instructions to control the operation of the nucleic acid loading device 1000, for example, to implement nucleic acid loading test.

The nucleic acid loading includes a process of connecting a nucleic acid sequence to a solid-phase substrate. The nucleic acid sequence may be DNA and/or RNA, or may be single-stranded and/or double-stranded and/or a complex containing a single-stranded or double-stranded nucleic acid sequence. The solid-phase substrate may be any solid support that can be used to attach/immobilize the nucleic acid sequence, such as nylon membranes, glass sheets, plastics, silicon wafers, magnetic beads, and the like. The glass may be ordinary glass, quartz glass, ordinary glass containing a metal coating, or quartz glass containing a metal coating.

Figure 4:
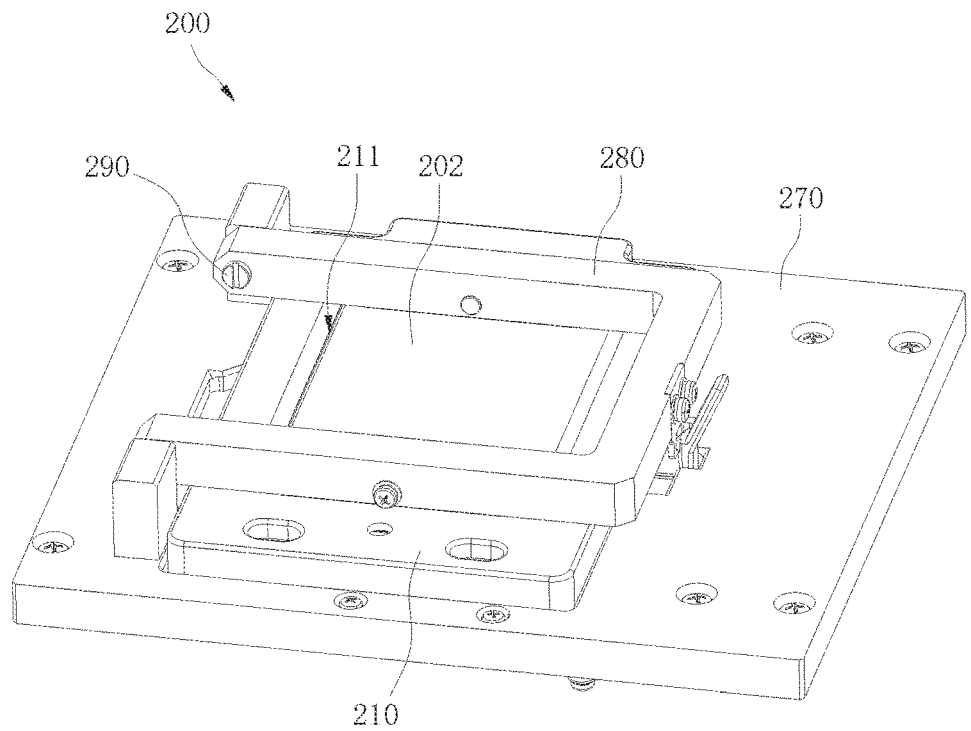
FIG. 4 illustrates a perspective view of a carrying module according to an embodiment of the present disclosure.
Figure 5:
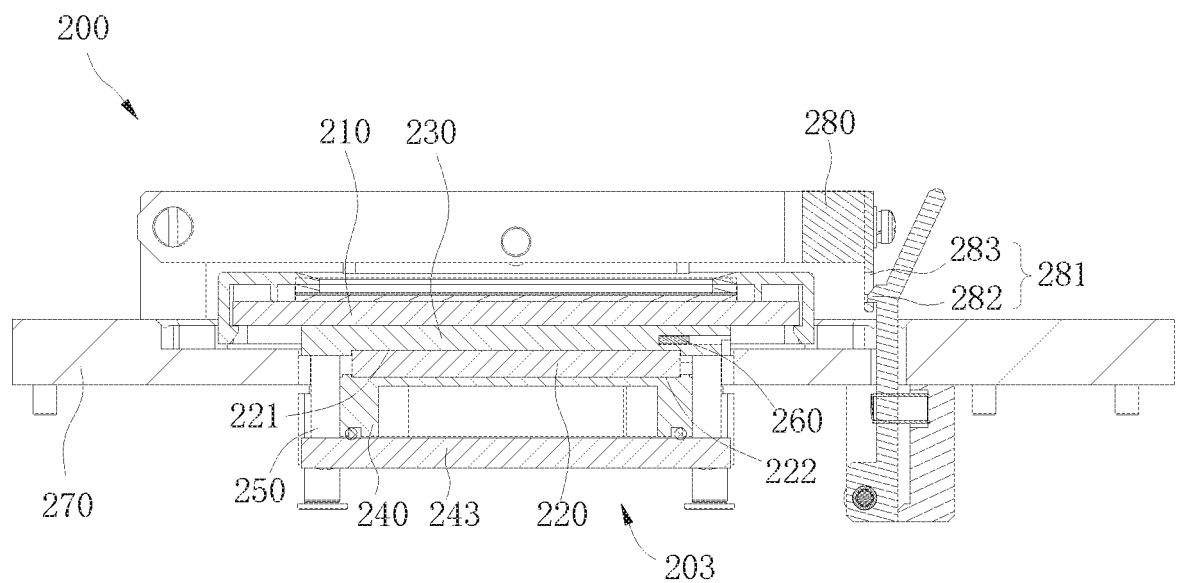
FIG. 5 illustrates a sectional view of a carrying module according to an embodiment of the present disclosure.
Figure 6:
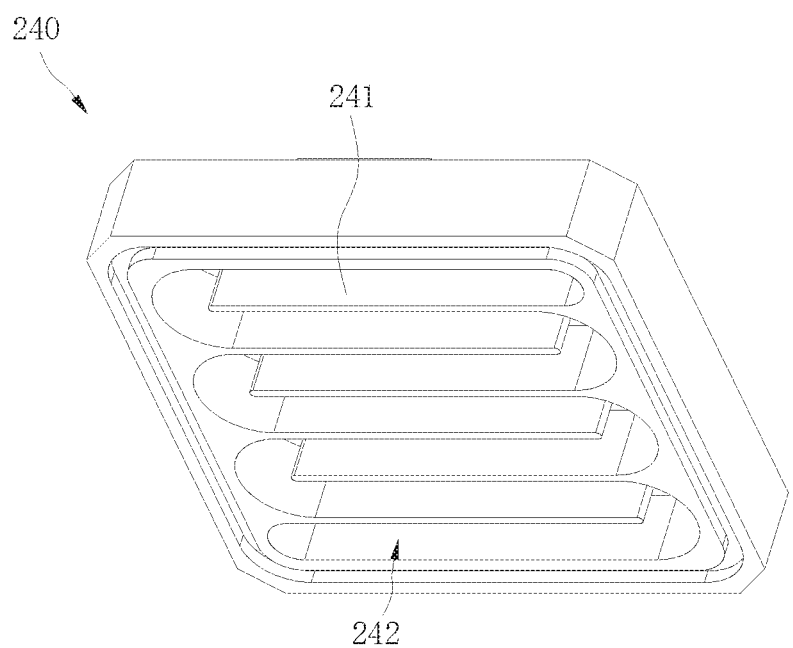
FIG. 6 illustrates a perspective view of a heat dissipating body according to an embodiment of the present disclosure.

Referring to FIGS. 4-6, the carrying module 200 includes an accommodating seat 210, a temperature control unit 203, an insulating body 250, a temperature sensor 260, a fixing seat 270, a pressing member 280 and a stop member 290. The temperature control unit 203 includes a semiconductor cooler 220, a heat conducting body 230, and a heat dissipating body 240.

The accommodating seat 210 is used to place a reactor 202. The panel 120 is provided with a first window 121 corresponding to the carrying module 200 (see FIG. 1), and the first window 121 is used to place the reactor 202 on the accommodating seat 210. The accommodating seat 210 exhibits a shape of a substantially rectangular parallelepiped and the accommodating seat 210 is provided with an accommodating groove 211 used to accommodate the reactor 202. A reagent may be pumped into the reactor 202 in the accommodating groove 211 for reaction. For example, performing reactions such as hybridization or immobilization in the reactor 202 placed on the accommodating groove 211. It could be understood that the accommodating seat 210 may be provided with a through-hole in communication with the accommodating groove 211, and the reagent can enter the accommodating groove 211 from the through-hole.

It should be noted that the reactor 202 may refer to a chip without a probe fixed thereon (i.e., a no-load chip), or a chip with a probe fixed thereon, or a reaction chip loaded with a nucleic acid molecule sample.

The reactor 202 includes the above solid-phase substrate. In one example, the reactor 202 is a chip which is a glass sheet with chemical groups on its surface. The probe/primer (oligonucleotide) is immobilized on the surface of the chip by the above nucleic acid loading device 1000 to implement the above nucleic acid loading. The nucleic acid loading belongs to immobilization reactions generally referred to in the field of biochemistry.

In one example, the reactor 202 is a chip which is a glass sheet with a first nucleic acid sequence attached on its surface. A second nucleic acid sequence is added to the above surface of the chip by the above nucleic acid loading device 1000, and at least a part of the second nucleic acid sequence is bound to the first nucleic acid sequence. In one specific example, the first nucleic acid sequence is a probe, and the second nucleic acid sequence is a nucleic acid sequence to be detected. The nucleic acid loading process belongs to hybridization reactions generally referred to in the field of biochemistry.

The above immobilization and/or hybridization reactions generally include a plurality of steps, such as preheating the reactor 202 and/or a first reagent, introducing the first reagent into the reactor 202 for a incorporation/ligation reaction (e.g., base pairing), introducing a second reagent into the reactor 202 at a certain flow rate to perform cleaning, after the incorporation/ligation reaction is finished, and the like. The first reagent may be one or more reagents containing a substrate. It could be understood that the device can be used to automate all the steps of a certain biochemical reaction, and can also be used to automate some steps of a certain biochemical reaction.

The nucleic acid loading device 1000 according to the embodiment of the present disclosure is a sample processing device, which can achieve the function of immobilizing the probe to the chip, and can bind, through hybridization, the sample to the chip with the probe immobilized on the surface, and can also sequence the sample to be detected.

The semiconductor cooler 220 includes a first face 221 and a second face 222 opposite to each other. The semiconductor cooler 220 starts to work after being electrified. At this time, one of the first face 221 and the second face 222 starts to refrigerate and the other one thereof starts to heat. For example, when the semiconductor cooler 220 works, the first face 221 starts to refrigerate, and the second face 222 starts to heat. It could be understood that when the working current of the semiconductor cooler 220 is changed, the refrigeration type of the first face 221 is changed. For example, when the working current of the semiconductor cooler 220 is forward, the first face 221 refrigerates; when the working current of the semiconductor cooler 220 is reverse, the first face 221 heats. Compared with other refrigerating elements, the semiconductor cooler 220 has advantages of being more environmentally friendly and noiseless.

The heat conducting body 230 is connected with the first face 221 and the accommodating seat 210. In such a way, the heat conducting body 230 can transmit heat of the semiconductor cooler 220 to the accommodating seat 210, such that the reactor 202 placed thereon can provide different temperatures. In order to make the heat conducting body 230 better transmit the heat to the accommodating seat 210 or the reactor 202, a paste material with good heat conductivity, such as silicone grease, is applied between the heat conducting body 230 and the accommodating seat 210, and/or between the heat conducting body 230 and the first face 221. Preferably, the material of the heat conducting body 230 is metal. The heat conducting body 230 is in a substantially rectangular parallelepiped shape, and the cross-sectional dimension of the heat conducting body 230 is substantially the same as that of the semiconductor cooler 220, such that the structural cooperation between the heat conducting body 230 and the semiconductor cooler 220 is more compact.

The heat dissipating body 240 is connected with the second face 222. For example, the heat dissipating body 240 is connected with the second face 222 through a paste material with good heat conductivity, such as silicone grease. In such a way, the heat dissipating body 240 may quickly dissipate the heat of the second face 222 to the outside of the semiconductor cooler 220, so as to improve working efficiency of the semiconductor cooler 220. The material of the heat dissipating body 240 is metal. For example, the material of the heat dissipating body 240 is copper, aluminum and the like. Preferably, the heat dissipating body 240 is formed with a plurality of spaced fins 241. The plurality of fins 241 can increase a surface area of the heat dissipating body 240, thereby improving the heat dissipation performance of the heat dissipating body 240.

In the present embodiment, the plurality of fins 241 define a heat dissipating channel 242 which is configured for cooling liquid to flow through. The carrying module 200 includes a cover plate 243, the cover plate 243 covers the heat dissipating channel 242, and the cover plate 243 is sealedly connected with the heat dissipating body 240. In such a way, the cooling liquid may transmit the heat of the heat dissipating body 240 to the outside of the heat dissipating body 240, so as to lower the temperature of the heat dissipating body 240. A sealing ring may be arranged between the cover plate 243 and the heat dissipating body 240, and the sealing ring can seal a gap between the cover plate 243 and the heat dissipating body 240.

Furthermore, the heat dissipating channel 242 is in a meandering shape, such that the total length of the heat dissipating channel 242 can be increased, and the heat dissipation effect of the heat dissipating body 240 is better.

The insulating body 250 is fixedly connected with the cover plate 243 and the heat conducting body 230, so as to avoid any short circuit between the cover plate 243 and the heat conducting body 230. The material of the insulating body 250 is an insulating material such as rubber.

The temperature sensor 260 is provided in the heat conducting body 230, and configured to detect the temperature of the heat conducting body 230. For example, the temperature sensor 260 is inserted into the heat conducting body 230 from one side of the heat conducting body 230. The control module 800 can control the working process of the semiconductor cooler 220 based on the temperature detected by the temperature sensor 260. In one example, when the temperature of the heat conducting body 230 detected by the temperature sensor 260 is lower than a target temperature, the control module 800 can control to increase the working current of the semiconductor cooler 220 to improve the power of the semiconductor cooler 220, such that the semiconductor cooler 220 can raise the temperature of the heat conducting body 230. In the present embodiment, the temperature sensor 260 is a contact temperature sensor, that is, the temperature sensor 260 is in contact with the heat conducting body 230. Certainly, the temperature sensor 260 may be a non-contact temperature sensor. For example, the temperature sensor 260 is an infrared temperature sensor.

The fixing seat 270 is fixed on the partition plate 130. For example, the fixing seat 270 is fixed on the partition plate 130 by a fastener such as a screw or a bolt and the like. The pressing member 280 is rotatably arranged on the fixing seat 270, and the accommodating seat 210 is fixed on the fixing seat 270. The pressing member 280 is connected with the fixing seat 270 by an engaging structure 281 so as to press the reactor 202 on the accommodating seat 210. In such a way, the reactor 202 can be stationary relative to the position of the fixing seat 270 to improve the stability of the position of the reactor 202.

In the present embodiment, the accommodating seat 210 is partially located in the fixing seat 270, and the heat dissipating body 240 is arranged below the fixing seat 270. The pressing member 280 exhibits a frame shape, and a rotating shaft of the pressing member 280 and the engaging structure 281 are located at two opposite ends of the pressing member 280, such that the engaging structure 281 can provide the pressing member 280 with a more stable force to press the reactor 202.

Specifically, in the present embodiment, the engaging structure 281 includes a protrusion 282 provided on the fixing seat 271 and an engaging hole formed in the pressing member 280. The protrusion 282 is engaged in the engaging hole 283. It could be understood that, after the pressing member 280 presses the reactor 202, the protrusion is snapped into the engaging hole 283, such that the position of the pressing member 280 is fixed to press the reactor 202 constantly. When the reactor 202 needs to be removed, the protrusion 282 is separated from the engaging hole 283, and then the pressing member 280 is rotated, such that the reactor 202 can be removed. The loading and unloading process of the reactor 202 is simple and the operation is convenient.

It could be understood that in other embodiments, the engaging structure includes a protrusion provided on the pressing member and an engaging hole formed in the fixing seat, and the protrusion is engaged in the engaging hole.

The stop member 290 is connected with the fixing seat 270 and the pressing member 280, and configured to limit a rotating angle of the pressing member 280 relative to the fixing seat 270. The stop member 290 is a columnar element such as a screw, and the stop member 290 passes through the pressing member and extends into the fixing seat 270. The stop member 290 can increase a frictional force on contact surfaces between the fixing seat 270 and the pressing member 280, such that the pressing member 280 keeps stationary after rotating at any angle relative to the fixing seat 270.

Figure 7:
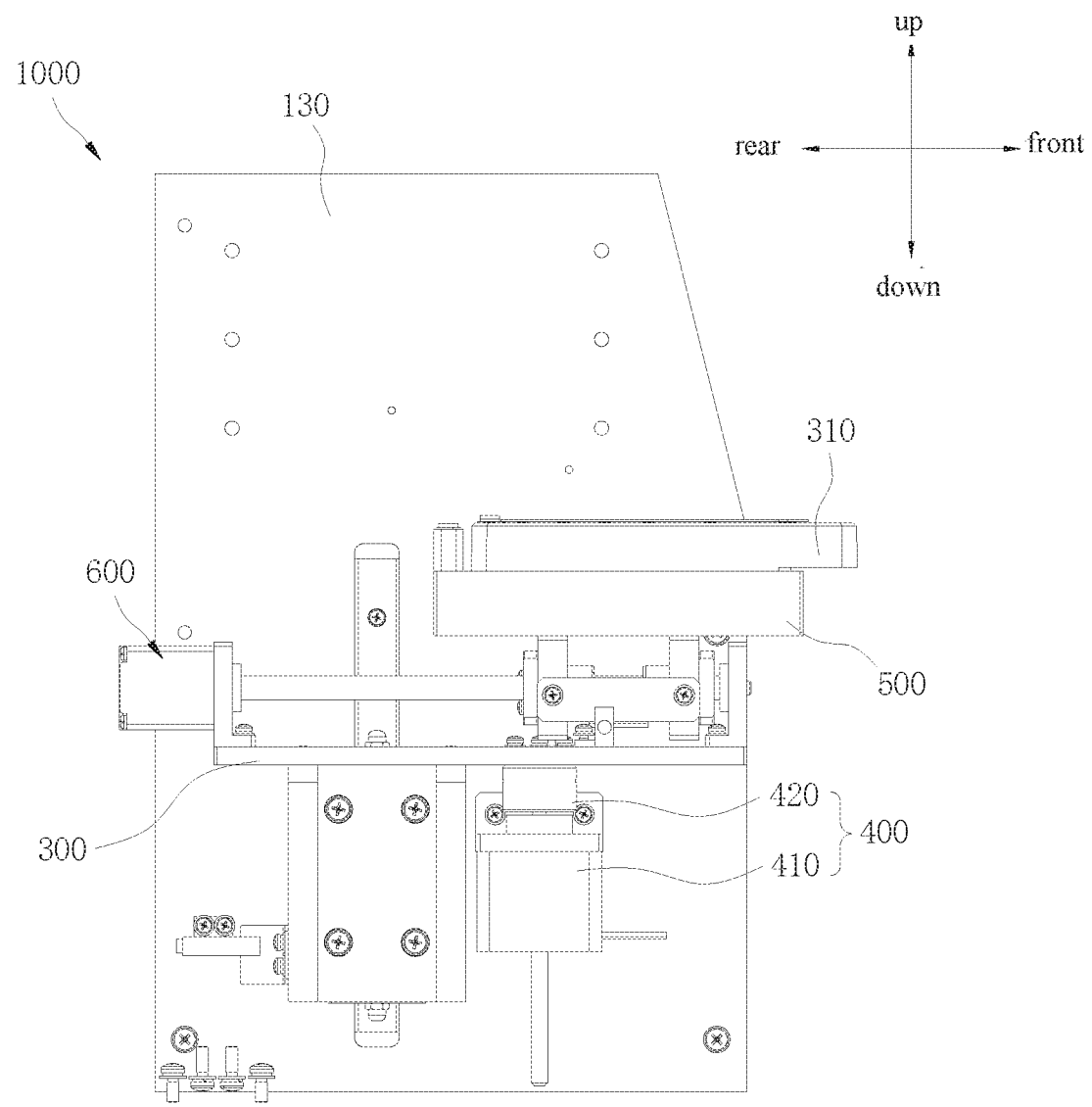
FIG. 7 illustrates a plan view of a partial structure of a sample processing device according to an embodiment of the present disclosure.
Figure 8:
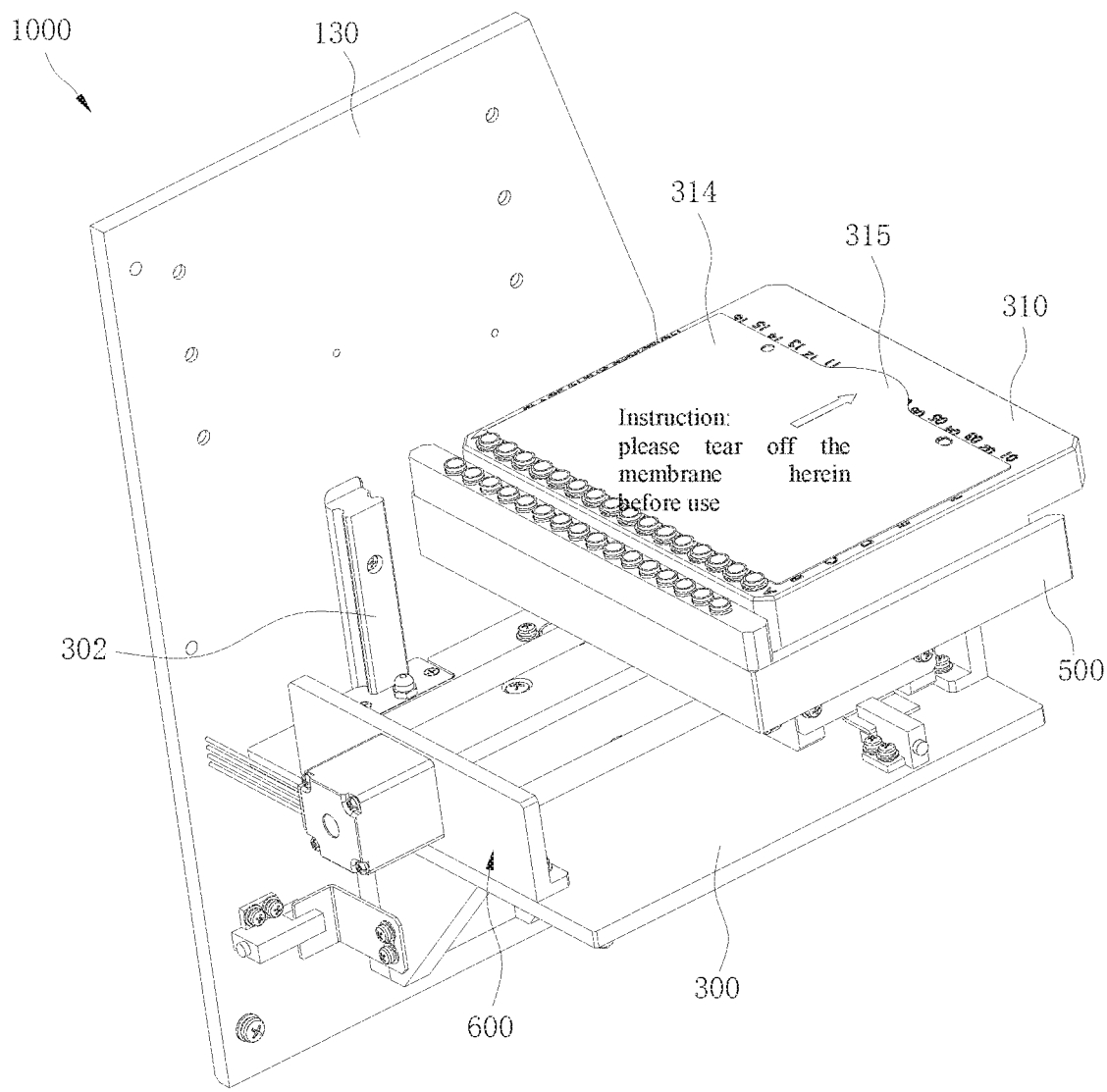
FIG. 8 illustrates a perspective view of a partial structure of a sample processing device according to an embodiment of the present disclosure.
Figure 9:
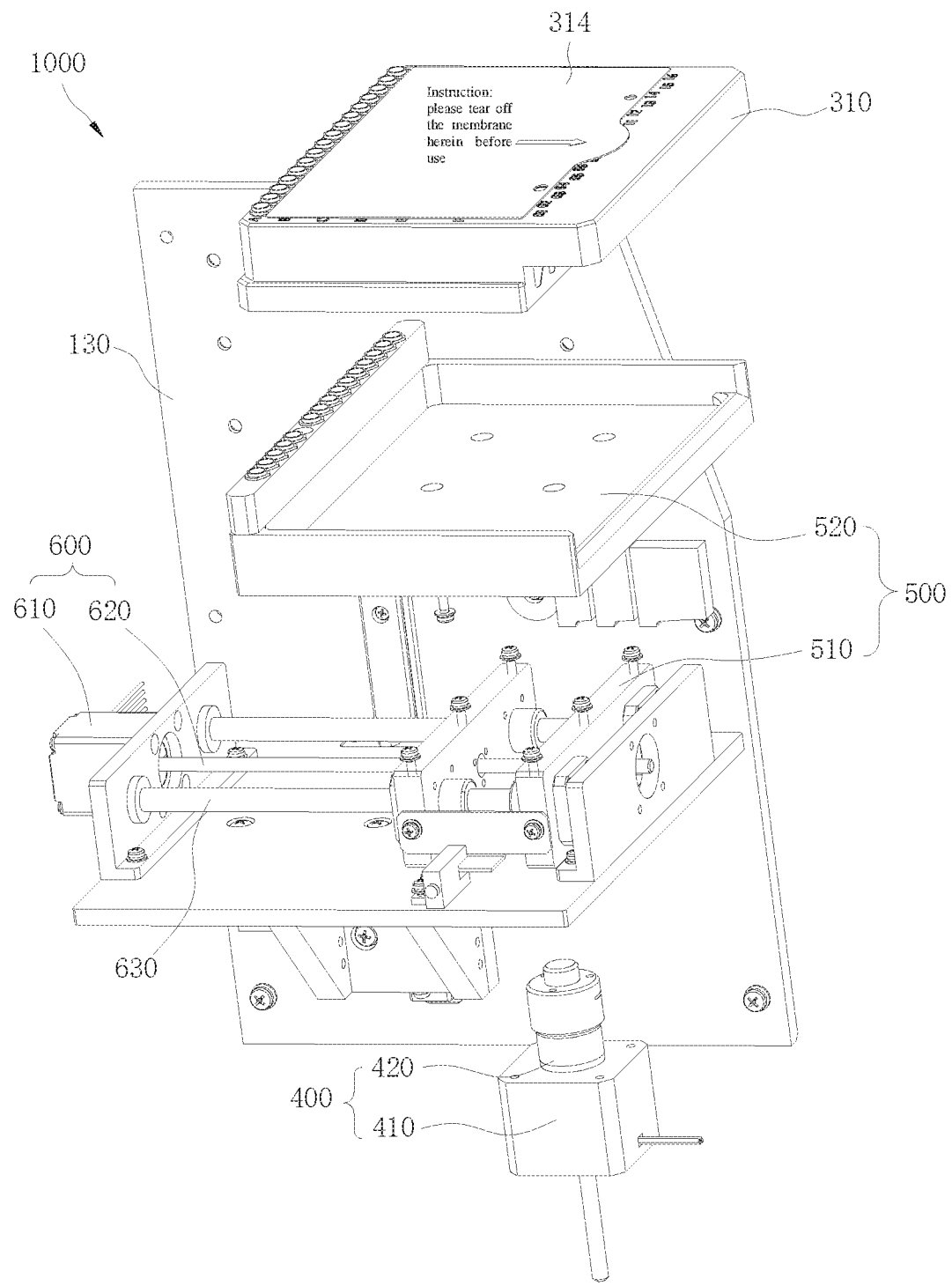
FIG. 9 illustrates an exploded view of a partial structure of a sample processing device according to an embodiment of the present disclosure.

Referring to FIGS. 7-9, the support platform 300 may be movably arranged on the partition plate 130. For example, the support platform 300 is arranged on the partition plate 130 through a guide rail. The support platform 300 is used to connect a reagent kit 310, and the reagent kit 310 is used to connect the reactor 202. For example, the reagent kit 310 may be connected to the reactor 202 through a conduit, thereby providing a reagent for the reactor 202.

The reagent kit 310 is a container for carrying a reagent which may be a liquid, solid and/or gaseous reagent. One or more reagent kits 310 may be provided, and one reagent kit 310 may accommodate one or more reagent bottles. In one example, the reagent kit 310 is provided with a plurality of positions for accommodating reagent bottles, and different reagent bottles may be used to store different reagents.

The first driving mechanism 400 is fixed on the partition plate 130, and configured to drive the support platform 300 to move along a first direction relative to the partition plate 130. As illustrated by the orientation in FIG. 7, the first direction is an up-down direction. In the present embodiment, the first driving mechanism 400 is located under the support platform 300, and the first driving mechanism 400 pushes the support platform 300 to move upward or pulls the support platform 300 to move downward. It could be understood that the reagent kit 310 may move with the movement of the support platform 300, which helps to switch among different reagents such that one or more reagents may enter the liquid circuit module 702 in sequence and/or together.

Specifically, the first driving mechanism 400 includes a first electric motor 410 fixed on the partition plate 130 and a first transmission shaft 420 connected with the first electric motor 410. The first transmission shaft 420 is connected with the support platform 300, and the first electric motor 410 is used to drive the first transmission shaft 420 to move so as to drive the support platform 300 to move relative to the partition plate 130.

For example, the first electric motor 410 is a stepping motor or a servo motor, such that the control module 800 can accurately control the working process of the first electric motor 410. Preferably, the first electric motor 410 is a through shaft motor. That is, the first transmission shaft 420 runs through the first electric motor 410, such that the structure of the nucleic acid loading device 1000 is more compact in the up-down direction.

For example, the first transmission shaft 420 is a screw rod. It could be understood that when the first electric motor 410 drives the screw rod to rotate, the screw rod may move up or down while rotating, so as to drive the support platform 300 to move relative to the partition plate 130.

The carrying member 500 is used to carry the reagent kit 310. The second driving mechanism 600 is fixed on the support platform 300, and the second driving mechanism 600 is used to drive the carrying member 500 to move along a second direction relative to the support platform 300, in which the second direction is perpendicular to the first direction. In the present embodiment, for example, the second direction is a front-rear direction as illustrated in FIG. 7. It could be understood that the reagent kit 310 may move along the second direction along with the carrying member 500. In such a way, the reagent kit 310 can move in the first direction and the second direction, and that is, the reagent kit 310 can move along the up-down direction and the front-rear direction.

Specifically, the second driving mechanism 600 includes a second electric motor 610 and a second transmission shaft 620, and the second electric motor 610 is fixed on the support platform 300. The second transmission shaft 620 is connected to the second electric motor 610. The carrying member 500 is fitted over the second transmission shaft 620, and the second electric motor 610 is used to drive the second transmission shaft 620 to rotate so as to drive the carrying member 500 to move along the second direction. In one example, the second transmission shaft 620 is a screw rod. The carrying member 500 is provided with a screw hole fitted with the screw rod, and the rotation of the screw rod may push the carrying member 500 to move by the threaded fit.

Specifically, the carrying member 500 includes a sliding block 510 and a bracket 520, and the sliding block 510 is fitted over the second transmission shaft 620. The bracket 520 is fixedly connected with the sliding block 510, and the bracket 520 is used to carry the reagent kit 310. The second electric motor 610 is connected with a guide rod 630 parallel to the second transmission shaft 620, and the guide rod 630 passes through the sliding block 510. The guide rod 630 can guide the carrying member 500 to move, thereby ensuring more stable movement of the carrying member 500.

The injection pump 700 is used to provide negative pressure for the reactor 202 to allow the reagent in the reagent kit 310 to flow to the reactor 202. The advantage of feeding liquid by using the negative pressure over feeding liquid by using positive pressure is obvious, that is, no need to worry about failures such as tube burst caused by blockage of fluid pipeline. When the reactor 202 is made of fragile materials such as glass or silicon wafers, the use of positive pressure to feed liquid may cause the glass or silicon wafers to burst.

It should be noted that a plurality of injection pumps 700 may be provided, and different injection pumps 700 can control different reagents to flow into the reactor 202.

Figure 10:
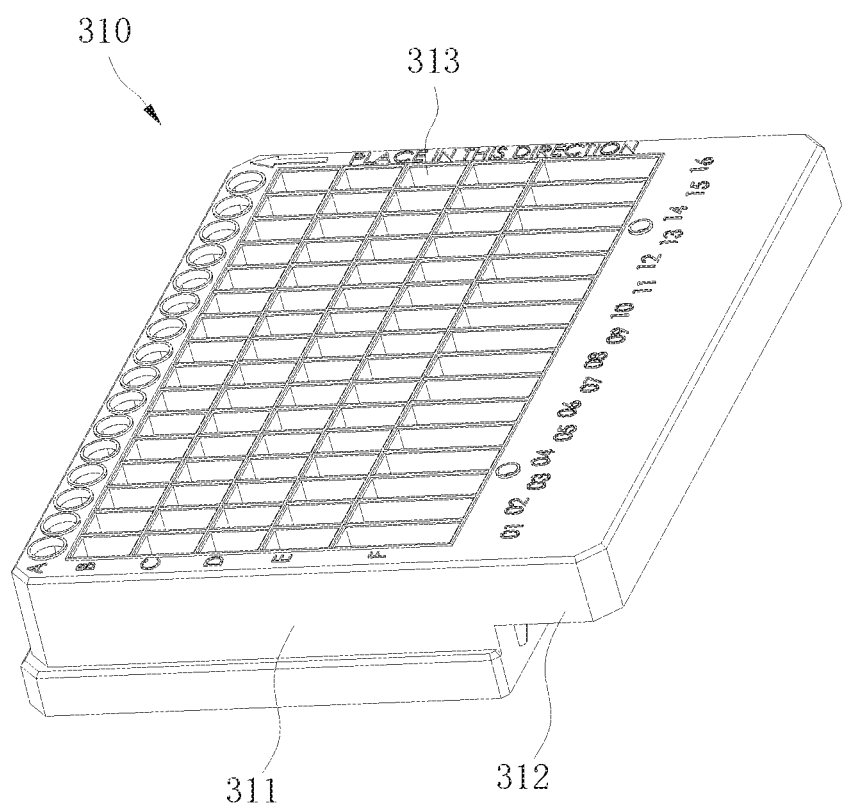
FIG. 10 illustrates a perspective view of a reagent kit according to an embodiment of the present disclosure.
Figure 11:
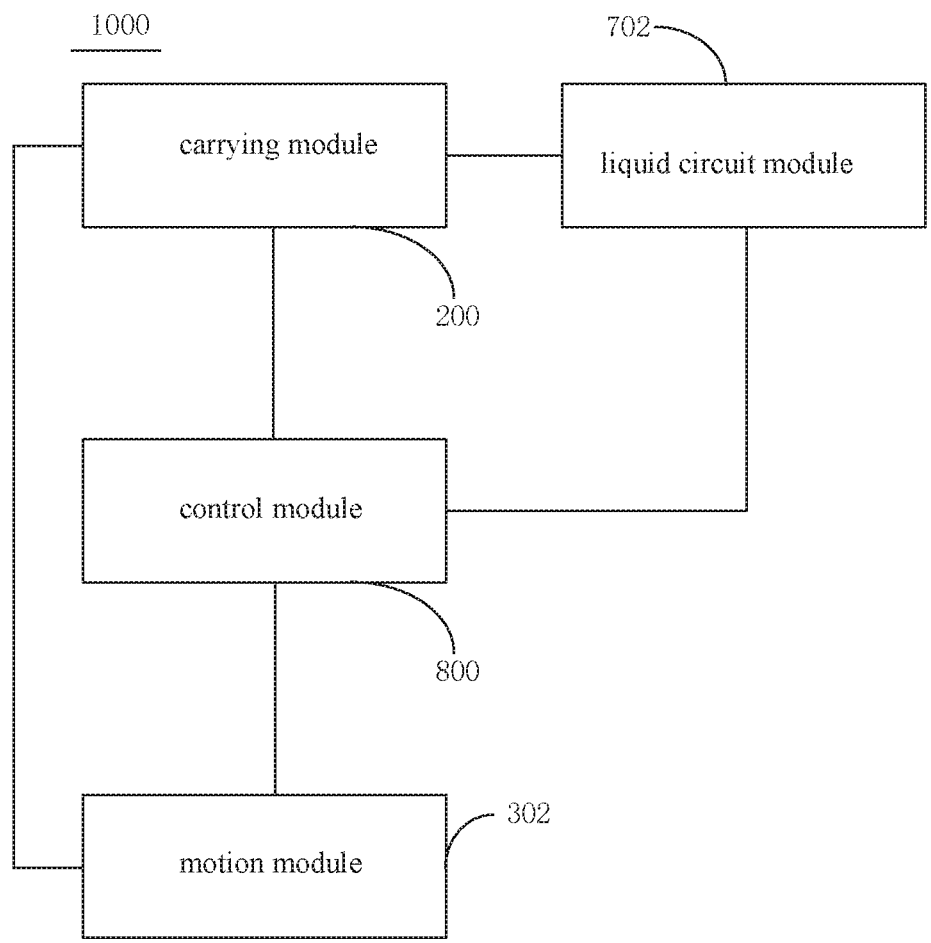
FIG. 11 illustrates a block diagram of a sample processing device according to an embodiment of the present disclosure.

Referring to FIGS. 8 and 10, the reagent kit 310 includes a liquid reservoir portion 311 and a handle portion 312 connected with the liquid reservoir portion 311. The liquid reservoir portion 311 is formed with a plurality of liquid reservoir grooves 313 in which the reagents may be stored. The handle portion 312 is convenient for the user to take the reagent kit 310. In one example, the panel 120 is provided with a second window 122 through which the reagent kit 310 can pass, and the user can hold the handle portion 312 and place the reagent kit 310 on the carrying member 500 through the second window 122. The reagent kit 310 is provided with a membrane 314 covering the plurality of liquid reservoir grooves 313, and the membrane 314 is used to seal the liquid reservoir grooves 313. The membrane 314 protrudes toward the handle portion 312 to form a flange 315, and the flange 315 enables the user to tear off the membrane 314 from the reagent kit 310 conveniently after the reagent kit 310 is placed on the carrying member 500.

In one example, the operation process of the nucleic acid loading device 1000 is as follows: first, the reactor 202 and the reagent kit 310 containing the first reagent are mounted on the accommodating seat 210 and the machine carrying member 500 respectively; then the control module 800 controls the injection pump 700 to provide the reactor 202 with negative pressure, to allow the reagent in the reagent kit 310 to flow to the reactor 202; the control module 800 controls the power of the semiconductor cooler 220 so that the reactor 202 reaches a predetermined temperature for a biochemical reaction; after the preset reaction time is reached, the control module 800 controls the motion module 302 to switch the reagents and controls the injection pump 700 to make the second reagent in the reagent kit 310 flow to the reactor 202, such that the first reagent in the reactor 202 flows out of the reactor 202 at a specific speed; after the preset time is reached, the reactor 202 may be removed from the accommodating seat 210.

To sum up, the nucleic acid loading device 1000 includes the carrying module 200, the motion module 302, the liquid circuit module 702 and the control module 800.

The carrying module 200 includes the accommodating seat 210 and the temperature control unit 203. The accommodating seat 210 is used to place the reactor 202, and the nucleic acid is loaded into the reactor 202. The temperature control unit 203 includes the semiconductor cooler 220, the heat conducting body 230 and the temperature sensor 260. The semiconductor cooler 220 includes the first face 221 and the second face 222 opposite to each other. The heat conducting body 230 is connected with the first face 221 and the accommodating seat 210. The temperature sensor 260 is provided in the heat conducting body 230, and used to detect the temperature of the heat conducting body 230.

The motion module 302 includes the partition plate 130, the support platform 300, the first driving mechanism 400, the carrying member 500 and the second driving mechanism 600. The support platform 300 is detachably and movably arranged on the partition plate 130. The first driving mechanism 400 is fixed on the partition plate 130, and the first driving mechanism 400 is used to drive the support platform 300 to move along the first direction relative to the partition plate 130. The second driving mechanism 600 is fixed on the support platform 300, and the second driving mechanism 600 is used to drive the carrying member 500 to move along the second direction relative to the support platform 300. The second direction is perpendicular to the first direction.

The liquid circuit module 702 is used to control reagents to flow into and out of the reactor 202. The liquid circuit module 702 includes the injection pump 700, and the injection pump is used to provide negative pressure for the reactor 202 to allow reagents to flow to the reactor 202.

The control module 800 is connected with the carrying module 200, the motion module 302 and the liquid circuit module 702. The control module 800 is configured to control the work of the first driving mechanism 400 and the second driving mechanism 600 and control the operation of the liquid circuit module 70 and the temperature control unit 203.

In the nucleic acid loading device 1000 according to one embodiment of the present disclosure, the first face 221 of the semiconductor cooler 220 heats or refrigerates during operation, thereby providing heat for the accommodating seat 210 through the heat conducting body 230, such that the reactor 202 can be at different ambient temperatures. In addition, the cooperation between the motion module 302 and the liquid circuit module 702 can achieve automation and industrialization of the process of loading the sample to be detected into the reactor 202. Furthermore, the nucleic acid loading device 1000 adopts a modular design, which is easier to industrialize.

It could be understood that the control module 800 may control the first driving mechanism 400 to drive the support platform 300 to move along the first direction relative to the partition plate 130; the control module 800 may control and drive the carrying member 500 to move along the second direction relative to the support platform 300; and the control module 800 may also control the injection pump 700 to provide negative pressure for the reactor 202.

Generally, the accuracy of the temperature detection by the temperature sensor 260 is affected by the ambient temperature, the size and material temperature coefficient of the load (such as the accommodating seat 210, the reactor 202, etc.), the mounting position of the temperature sensor 260, the material and size of the semiconductor cooler 220, the aging of the temperature control unit 203, and the like; moreover, the temperature sensor 260 has problems of zero drift and temperature drift. It could be understood that in the nucleic acid loading device 1000, the temperature sensor 260 functions as a temperature acquisition apparatus and is intended to acquire and reflect the temperature of the reactor 202 or the load.

In some embodiments, the temperature sensor 260 is a calibrated temperature sensor, and the temperature y detected by the temperature sensor 260 meets a polynomial equation $$y = \sum_{i=0}^{n} a_i x^i,$$

wherein n is a natural number and satisfies 4≤n≤6, x is the temperature detected by the temperature sensor 260 before calibration, and $a_i$ is the polynomial coefficient.

In some embodiments, the control module 800 includes a machine-executable program, and executing the machine-executable program includes calibrating the temperature sensor 260 by using the following polynomial equation, and the temperature y detected by the calibrated temperature sensor 260 meets $$y = \sum_{i=0}^{n} a_i x^i,$$

wherein n is a natural number and satisfies 4≤n≤6, x is the temperature detected by the temperature sensor before calibration, and $a_i$ is the polynomial coefficient.

In one example, the temperature sensor 260 is a digital output type sensor, and the above offset is eliminated by a software program. For example, if the required reaction temperature is within the range of 10–70° C., the following polynomial may be used to calibrate the temperature output by the temperature sensor 260: $y=-1.7345e^{-7}*x^4-3.1059e^{-5}*x^3+0.0001456*x^2+1.0044*x+6.032$, as illustrated in drawings.

In the nucleic acid loading device 1000, in the range of 10–30° C., the linear relation y=1.004x+6.032 may be basically used to eliminate the temperature offset.

The shown equation may be established based on a series of temperature values detected by the temperature sensor to be calibrated and the calibrated temperature sensor. For example, the reactor 202 is placed on the accommodating seat 210, and a calibrated temperature sensor is placed in the reactor 202. Supposing the temperatures detected by the temperature sensor to be calibrated in the device are 10° C., 15° C., 20° C., 25° C., 30° C., 35° C., 40° C., 45° C., 50° C., 55° C., 60° C., 65° C. and 70° C., the corresponding temperature values detected by the calibrated temperature sensor are 16.10° C., 20.90° C., 25.80° C., 31.21° C., 35.02° C., 39.55° C., 44.05° C., 48.21° C., 51.50° C., 55.03° C., 58° C., 60.07° C. and 62.33° C., respectively. Based on these two groups of the temperature values, the relation can be fitted to obtain the polynomial equation.

Referring to FIG. 1, in some embodiments, the nucleic acid loading device 1000 also includes a display screen 900, and the control module 800 is used to control the display screen 900 to display the current temperature of the accommodating seat 210.

Reference throughout this specification to "one embodiment", "some embodiments", "an embodiment", "a specific example" or "some examples", means that a particular feature, structure, material, or characteristic described in connection with the embodiment or example is included in at least one embodiment or example of the present disclosure. Thus, the appearances of the phrases in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated that the above embodiments are explanatory and cannot be construed to limit the present disclosure, and changes, alternatives, and modifications can be made in the embodiments without departing from scope of the present disclosure by those skilled in the art.

Although the principles herein have been shown in various embodiments, many modifications of structures, arrangements, ratios, elements, materials, and components that are particularly suitable for specific environments and operating requirements can be made without departing from the principles and scope of this disclosure use. The above modifications and other changes or amendments will be included within the scope of the present disclosure.

The foregoing specific description has been described with reference to various embodiments. However, those skilled in the art can understand that various modifications and changes can be made without departing from the scope of the present disclosure. Therefore, consideration of this disclosure will be in an illustrative rather than a restrictive sense, and all such modifications will be included within its scope. Likewise, there have been the advantages, various other advantages, and solutions to the problems of the various embodiments described above. However, benefits, advantages, solutions to problems, and any elements that can produce these, or solutions that make them more explicit, should not be interpreted as critical, necessary, or necessary. The term "comprising" and any other variants used in this article are non-exclusive, so that a process, method, article, or device that includes a list of elements includes not only these elements, but also those that are not explicitly listed or do not belong to the process, methods, systems, articles or other elements of equipment. Furthermore, the term "coupled" and any other variations thereof used herein refer to physical connection, electrical connection, magnetic connection, optical connection, communication connection, functional connection, and/or any other connection.

Those skilled in the art can understand that many changes can be made to the details of the above-described embodiments without departing from the basic principles of the disclosure. Therefore, the scope of the present disclosure should be determined according to the following claims.

The invention claimed is:
1. A nucleic acid loading device, comprising:
a housing;
a carrying module in the housing comprising an accommodating seat and a temperature control unit, and a reactor detachably connected to the accommodating seat, wherein the reactor is a chip for receiving a nucleic acid molecule sample, the nucleic acid loading being performed in the reactor, the temperature control unit comprising a semiconductor cooler, a heat conducting body and a temperature sensor, the semiconductor cooler comprising a first face and a second face opposite to each other, the heat conducting body being connected to the first face and the accommodating seat, the temperature sensor being arranged in the heat conducting body, and the temperature sensor being configured to detect a temperature of the heat conducting body;

a motion module in the housing comprising a partition plate, a support platform, a first driving mechanism, a carrying member configured to carry a reagent container including a reagent, and a second driving mechanism, the support platform being detachably and movably arranged on the partition plate, the first driving mechanism being fixed on the partition plate and configured to drive the support platform to move along a first direction relative to the partition plate, the second driving mechanism being fixed on the support platform and configured to drive the carrying member to move along a second direction relative to the support platform, the second direction being perpendicular to the first direction;

a liquid circuit module in the housing configured to control the reagent to flow into and out of the reactor, and comprising a pump configured to provide negative pressure; and a control module in the housing connected with the carrying module, the motion module and the liquid circuit module, and configured to control operation of the first driving mechanism, the second driving mechanism, the liquid circuit module and the temperature control unit, wherein the partition plate separates the housing into first and second compartments with at least the pump and the control module in the first compartment and at least the carrying module, the support platform, the first driving mechanism, and the second driving mechanism in the second compartment.

2. The nucleic acid loading device as claimed in claim 1, wherein the temperature sensor is a calibrated temperature sensor, and a temperature y detected by the temperature sensor satisfies a polynomial equation $$y = \sum_{i=0}^{n} a_i x^i,$$

wherein n is a natural number and satisfies $4 \leq n \leq 6$, x is a temperature detected by the temperature sensor before calibration, $a_i$ is a polynomial coefficient.

3. The nucleic acid loading device as claimed in claim 1, wherein the control module comprises a machine-executable program, executing the machine-executable program comprises calibrating the temperature sensor by using the following polynomial equation, and the temperature y detected by the calibrated temperature sensor meets the $$y = \sum_{i=0}^{n} a_i x^i,$$

wherein:

n is a natural number and satisfies $4 \leq n \leq 6$, x is a temperature detected by the temperature sensor before calibration, $a_i$ is a polynomial coefficient.

4. The nucleic acid loading device as claimed in claim 1, wherein the first driving mechanism comprises a first electric motor fixed on the partition plate and a first transmission shaft connected with the first electric motor, the first transmission shaft is connected with the support platform, and the first electric motor is configured to drive the first transmission shaft to move so as to drive the support platform to move relative to the partition plate.

5. The nucleic acid loading device as claimed in claim 1, wherein the second driving mechanism comprises a second electric motor fixed on the support platform and a second transmission shaft connected with the second electric motor, the carrying member is fitted over the second transmission shaft, and the second electric motor is configured to drive the second transmission shaft to rotate so as to drive the carrying member to move along the second direction.

6. The nucleic acid loading device as claimed in claim 1, wherein the housing comprises a panel provided with a window over the carrying module.

7. The nucleic acid loading device as claimed in claim 1, further comprising the reagent container, wherein the support platform is detachably connected to the reagent container, the reagent container being connected to the reactor via a conduit.

8. The nucleic acid loading device as claimed in claim 1, wherein the second driving mechanism comprises a second electric motor fixed on the support platform and a second transmission shaft connected with the second electric motor, the carrying member is fitted over the second transmission shaft, and the second electric motor is configured to drive the second transmission shaft to rotate so as to drive the carrying member to move along the second direction.

9. The nucleic acid loading device as claimed in claim 1, wherein the pump is configured to provide negative pressure for the reactor to allow a reagent in the reagent container to flow to the reactor.

10. The nucleic acid loading device as claimed in claim 1, wherein the temperature control unit further comprises a heat dissipating body connected with the second face.

11. The nucleic acid loading device as claimed in claim 10, wherein the heat dissipating body is formed with a plurality of heat dissipating fins arranged at intervals.

12. The nucleic acid loading device as claimed in claim 11, wherein the plurality of heat dissipating fins define a heat dissipating channel configured for cooling liquid to flow through, the carrying module comprises a cover plate, the cover plate covers the heat dissipating channel, and the cover plate is sealedly connected with the heat dissipating body.

13. The nucleic acid loading device as claimed in claim 12, wherein the heat dissipating channel includes a plurality of bends.

14. The nucleic acid loading device as claimed in claim 12, wherein the carrying module comprises an insulating body fixedly connected with the cover plate and the heat conducting body.

15. The nucleic acid loading device as claimed in claim 1, wherein the carrying module comprises a fixing seat, on which the accommodation seat is fixed, and a pressing member having a proximal end rotatably arranged on the fixing seat such that the pressing member is rotatable between an open position and a pressing position in which the pressing member presses the reactor onto the accommodating seat, wherein a distal end of the pressing member is securable to the fixing seat in the pressing position by an engaging structure.

16. The nucleic acid loading device as claimed in claim 15, wherein the engaging structure comprises a protrusion provided on the fixing seat configured to engage with and an engaging hole in the pressing member; or the engaging structure comprising a protrusion on the pressing member configured to engage with an engaging hole in the fixing seat.

17. The nucleic acid loading device as claimed in claim 15, further comprising a stop member connected with the fixing seat and the pressing member and configured to limit a rotating angle of the pressing member relative to the fixing seat.

18. A method of nucleic acid immobilization and/or hybridization, including a step of immobilizing and/or hybridizing utilizing the nucleic acid loading device as claimed in claim 1.

* * * * *